(12) United States Patent
Pepper

(10) Patent No.: US 7,985,236 B2
(45) Date of Patent: *Jul. 26, 2011

(54) RAPID EXCHANGE BALLOON DILATION CATHETER HAVING REINFORCED MULTI-LUMEN DISTAL PORTION

(75) Inventor: Lanny R. Pepper, Larue, TX (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/480,949

(22) Filed: Jun. 9, 2009

(65) Prior Publication Data

US 2009/0247947 A1 Oct. 1, 2009

Related U.S. Application Data

(63) Continuation of application No. 11/174,676, filed on Jul. 5, 2005, now Pat. No. 7,544,201.

(51) Int. Cl.
*A61M 29/00* (2006.01)
(52) U.S. Cl. .......................... 606/194; 604/103
(58) Field of Classification Search ................. 604/103, 604/103.1, 103.4; 606/194
See application file for complete search history.

(56) References Cited

U.S. PATENT DOCUMENTS

| | | | |
|---|---|---|---|
| 1,596,284 A | 8/1926 | Malmgren |
| 2,043,083 A | 6/1936 | Wappler |
| 3,769,981 A | 11/1973 | McWhorter |
| 3,981,415 A | 9/1976 | Fowler et al. |
| 4,367,396 A | 1/1983 | Ravinsky |
| 4,482,516 A | 11/1984 | Bowman et al. |
| 4,572,186 A | 2/1986 | Gould et al. |
| 4,637,396 A | 1/1987 | Cook |
| 4,652,258 A | 3/1987 | Drach |
| 4,702,252 A | 10/1987 | Brooks |
| 4,704,130 A | 11/1987 | Gilding et al. |
| 4,706,670 A | 11/1987 | Andersen et al. |
| 4,748,982 A | 6/1988 | Horzewski et al. |
| 4,796,629 A | 1/1989 | Grayzel |
| 4,834,755 A | 5/1989 | Silvestrini et al. |
| 4,837,396 A | 6/1989 | Cook |
| 4,884,573 A | 12/1989 | Wijay et al. |
| 4,952,357 A | 8/1990 | Euteneuer |
| 4,983,167 A | 1/1991 | Sahota |

(Continued)

OTHER PUBLICATIONS

Nylon; Wikipedia, the free encyclopedia; Jun. 27, 2008; pp. 1-7; available at http://en.wikipedia.org/wiki/Nylon. Fiber; Wikipedia, the free encyclopedia; Jun. 27, 2008; pp. 1-3; available at http://en.wikipedia.org/wiki/Fiber.
Putnam Plastics Corporation; Putnam Plastics—Thermoset Polyimide Tubing; Mar. 20, 2005; available at www.putnamplastics.com.
Arkema Group; Pebax® Application Areas; Jun. 2000.

*Primary Examiner* — Nicolas D Lucchesi
*Assistant Examiner* — Victoria P Campbell
(74) *Attorney, Agent, or Firm* — King & Schickli, PLLC

(57) ABSTRACT

A rapid ex balloon dilation catheter includes a catheter shaft with a proximal tubular member defining a proximal inflation/deflation lumen for conveying fluids therethrough with a distal portion of the bore of proximal tubular member filled with a fluid-impervious barrier, a distal body extending from the fluid-impervious barrier to the distal end of the shaft, a plurality of distal tubular members defining distal inflation/deflation lumens in fluid communication with the proximal inflation/deflation lumen and extending through the fluid-impervious barrier and the distal body to the distal end of the shaft distal portion, a guidewire tubular member having a bore extending from a side aperture formed in the distal body through the distal body alongside the distal tubular members in a multi-lumen arrangement, and a plurality of stiffening members extending from within the fluid-impervious barrier into the distal body to a point within the shaft distal portion.

20 Claims, 6 Drawing Sheets

U.S. PATENT DOCUMENTS

| | | |
|---|---|---|
| 4,998,421 A | 3/1991 | Zafiroglu |
| 5,042,985 A | 8/1991 | Elliott et al. |
| 5,046,497 A | 9/1991 | Millar |
| 5,061,273 A | 10/1991 | Yock |
| 5,078,727 A | 1/1992 | Hannam et al. |
| 5,108,415 A | 4/1992 | Pinchuk et al. |
| 5,112,304 A | 5/1992 | Barlow et al. |
| 5,116,360 A | 5/1992 | Pinchuk et al. |
| 5,171,297 A | 12/1992 | Barlow et al. |
| 5,201,706 A | 4/1993 | Noguchi et al. |
| 5,207,700 A | 5/1993 | Euteneuer |
| 5,264,260 A | 11/1993 | Saab |
| 5,270,086 A | 12/1993 | Hamlin |
| 5,290,306 A | 3/1994 | Trotta et al. |
| 5,295,960 A | 3/1994 | Aliahmad et al. |
| 5,304,340 A | 4/1994 | Downey |
| 5,306,245 A | 4/1994 | Heaven |
| 5,306,246 A | 4/1994 | Sahatjian et al. |
| 5,314,443 A | 5/1994 | Rudnick |
| 5,330,429 A | 7/1994 | Noguchi et al. |
| 5,338,299 A | 8/1994 | Barlow |
| 5,344,401 A | 9/1994 | Radisch et al. |
| 5,358,486 A | 10/1994 | Saab |
| 5,410,797 A | 5/1995 | Steinke et al. |
| 5,451,209 A | 9/1995 | Ainsworth et al. |
| 5,451,233 A | 9/1995 | Yock |
| 5,464,394 A | 11/1995 | Miller et al. |
| 5,470,314 A | 11/1995 | Wallinsky |
| 5,477,886 A | 12/1995 | Van Beugen et al. |
| 5,478,320 A | 12/1995 | Trotta |
| 5,492,532 A | 2/1996 | Ryan et al. |
| 5,549,552 A | 8/1996 | Peters et al. |
| 5,549,556 A | 8/1996 | Ndondo-Lay et al. |
| 5,554,120 A | 9/1996 | Chen et al. |
| 5,575,771 A | 11/1996 | Walinsky |
| 5,587,125 A | 12/1996 | Roychowdhury |
| 5,599,576 A | 2/1997 | Opolski |
| 5,599,578 A | 2/1997 | Opolski |
| 5,620,649 A | 4/1997 | Trotta |
| 5,647,848 A | 7/1997 | Ole Jorgensen |
| 5,690,642 A | 11/1997 | Osborne et al. |
| 5,728,063 A | 3/1998 | Preissman et al. |
| 5,728,083 A | 3/1998 | Pressman et al. |
| 5,741,325 A | 4/1998 | Chaikof et al. |
| 5,752,934 A | 5/1998 | Campbell et al. |
| 5,755,690 A | 5/1998 | Saab |
| 5,759,172 A | 6/1998 | Weber et al. |
| 5,769,817 A | 6/1998 | Burgmeier |
| 5,772,681 A | 6/1998 | Leoni |
| 5,788,979 A | 8/1998 | Alt et al. |
| 5,797,877 A | 8/1998 | Hamilton et al. |
| 5,820,613 A | 10/1998 | Van Werven-Franssen et al. |
| 5,868,779 A | 2/1999 | Ruiz |
| 5,879,369 A | 3/1999 | Ishida |
| 5,928,181 A | 7/1999 | Coleman et al. |
| 5,972,441 A | 10/1999 | Campbell et al. |
| 5,980,486 A | 11/1999 | Enger |
| 6,007,544 A | 12/1999 | Kim |
| 6,010,480 A | 1/2000 | Abele et al. |
| 6,012,457 A | 1/2000 | Lesh |
| 6,015,430 A | 1/2000 | Wall |
| 6,024,740 A | 2/2000 | Lesh et al. |
| 6,024,772 A | 2/2000 | Rau et al. |
| 6,027,779 A | 2/2000 | Campbell et al. |
| 6,036,697 A | 3/2000 | DiCaprio |
| 6,036,715 A | 3/2000 | Yock |
| 6,117,101 A | 9/2000 | Diederich et al. |
| 6,124,007 A | 9/2000 | Wang et al. |
| 6,127,597 A | 10/2000 | Beyar et al. |
| 6,129,708 A | 10/2000 | Enger |
| 6,156,254 A | 12/2000 | Andrews et al. |
| 6,159,238 A | 12/2000 | Killion et al. |
| 6,164,283 A | 12/2000 | Lesh |
| 6,171,297 B1 | 1/2001 | Pedersen et al. |
| 6,183,492 B1 | 2/2001 | Hart et al. |
| 6,186,978 B1 | 2/2001 | Samson et al. |
| 6,187,013 B1 | 2/2001 | Stoltze et al. |
| 6,188,978 B1 | 2/2001 | Samson et al. |
| 6,213,995 B1 | 4/2001 | Steen et al. |
| 6,234,995 B1 | 5/2001 | Peacock, III |
| 6,245,064 B1 | 6/2001 | Lesh et al. |
| 6,254,599 B1 | 7/2001 | Lesh et al. |
| 6,263,236 B1 | 7/2001 | Kasinkas et al. |
| 6,270,902 B1 | 8/2001 | Tedeschi et al. |
| 6,290,485 B1 | 9/2001 | Wang |
| 6,305,378 B1 | 10/2001 | Lesh |
| 6,306,154 B1 | 10/2001 | Hudson et al. |
| 6,309,379 B1 | 10/2001 | Willard et al. |
| 6,315,751 B1 | 11/2001 | Cosgrove et al. |
| 6,328,925 B1 | 12/2001 | Wang et al. |
| 6,361,529 B1 | 3/2002 | Goodin et al. |
| 6,394,995 B1 | 5/2002 | Solar et al. |
| 6,544,219 B2 | 4/2003 | Happ et al. |
| 6,626,889 B1 | 9/2003 | Simpson et al. |
| 6,663,648 B1 | 12/2003 | Trotta |
| 6,702,750 B2 | 3/2004 | Yock |
| 6,702,782 B2 | 3/2004 | Miller et al. |
| 6,706,051 B2 | 3/2004 | Hudson et al. |
| 6,733,487 B2 | 5/2004 | Keith et al. |
| 6,743,196 B2 | 6/2004 | Barbut et al. |
| 6,746,425 B1 | 6/2004 | Beckham |
| 6,748,425 B1 | 6/2004 | Beckham |
| 6,755,845 B2 | 6/2004 | Kieturakis et al. |
| 6,761,708 B1 | 7/2004 | Chiu et al. |
| 6,899,713 B2 | 5/2005 | Shaolian et al. |
| 6,905,743 B1 | 6/2005 | Chen et al. |
| 6,911,038 B2 | 6/2005 | Mertens et al. |
| 6,942,680 B2 | 9/2005 | Grayzel et al. |
| 6,977,103 B2 | 12/2005 | Chen et al. |
| 7,252,650 B1 | 8/2007 | Andrews et al. |
| 7,300,415 B2 | 11/2007 | McMurtry et al. |
| 7,309,324 B2 | 12/2007 | Hayes et al. |
| 7,354,419 B2 | 4/2008 | Davies et al. |
| 7,435,254 B2 | 10/2008 | Chouinard et al. |
| 7,500,982 B2 | 3/2009 | Pepper |
| 7,544,201 B2 | 6/2009 | Pepper |
| 7,635,510 B2 | 12/2009 | Horn et al. |
| 7,662,163 B2 | 2/2010 | Grayzel et al. |
| 7,682,335 B2 | 3/2010 | Pepper et al. |
| 2002/0058960 A1 | 5/2002 | Hudson et al. |
| 2002/0077653 A1 | 6/2002 | Hudson et al. |
| 2002/0161388 A1 | 10/2002 | Samuels et al. |
| 2004/0015182 A1 | 1/2004 | Kieturakis et al. |
| 2004/0039332 A1 | 2/2004 | Kantor |
| 2004/0073163 A1 | 4/2004 | Tomaschko et al. |
| 2004/0073299 A1 | 4/2004 | Hudson et al. |
| 2004/0082965 A1 | 4/2004 | Beckham |
| 2004/0109964 A1 | 6/2004 | Beckham |
| 2004/0176740 A1 | 9/2004 | Chouinard |
| 2005/0027249 A1 | 2/2005 | Reifart et al. |
| 2005/0033225 A1 | 2/2005 | Wu et al. |
| 2005/0102020 A1 | 5/2005 | Grayzel et al. |
| 2005/0123702 A1 | 6/2005 | Beckham |
| 2005/0267408 A1 | 12/2005 | Grandt et al. |
| 2005/0271844 A1 | 12/2005 | Mapes et al. |
| 2006/0015133 A1 | 1/2006 | Grayzel et al. |
| 2006/0085022 A1 | 4/2006 | Hayes et al. |
| 2006/0085023 A1 | 4/2006 | Davies et al. |
| 2006/0085024 A1 | 4/2006 | Pepper et al. |
| 2007/0010847 A1 | 1/2007 | Pepper |
| 2007/0016133 A1 | 1/2007 | Pepper |
| 2007/0059466 A1 | 3/2007 | Beckham |
| 2007/0093865 A1 | 4/2007 | Beckham |
| 2007/0213760 A1 | 9/2007 | Hayes et al. |
| 2007/0219490 A1 | 9/2007 | Pepper et al. |
| 2008/0082050 A1 | 4/2008 | Solar et al. |
| 2008/0183132 A1 | 7/2008 | Davies et al. |
| 2008/0188805 A1 | 8/2008 | Davies et al. |
| 2009/0043254 A1 | 2/2009 | Pepper et al. |
| 2009/0171277 A1 | 7/2009 | Pepper |
| 2009/0247947 A1 | 10/2009 | Pepper |
| 2009/0294031 A1 | 12/2009 | Pepper et al. |
| 2010/0179581 A1 | 7/2010 | Beckham |

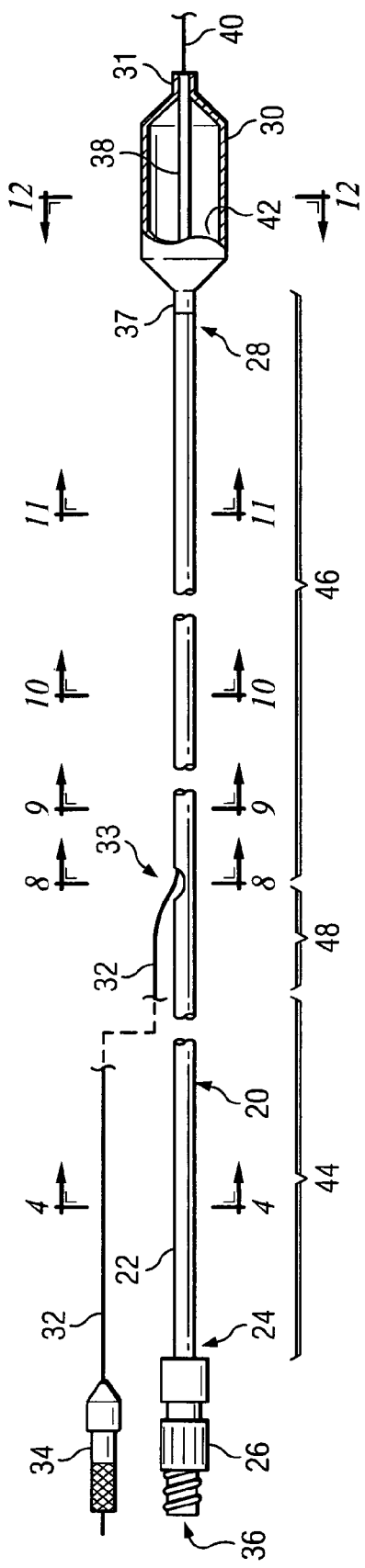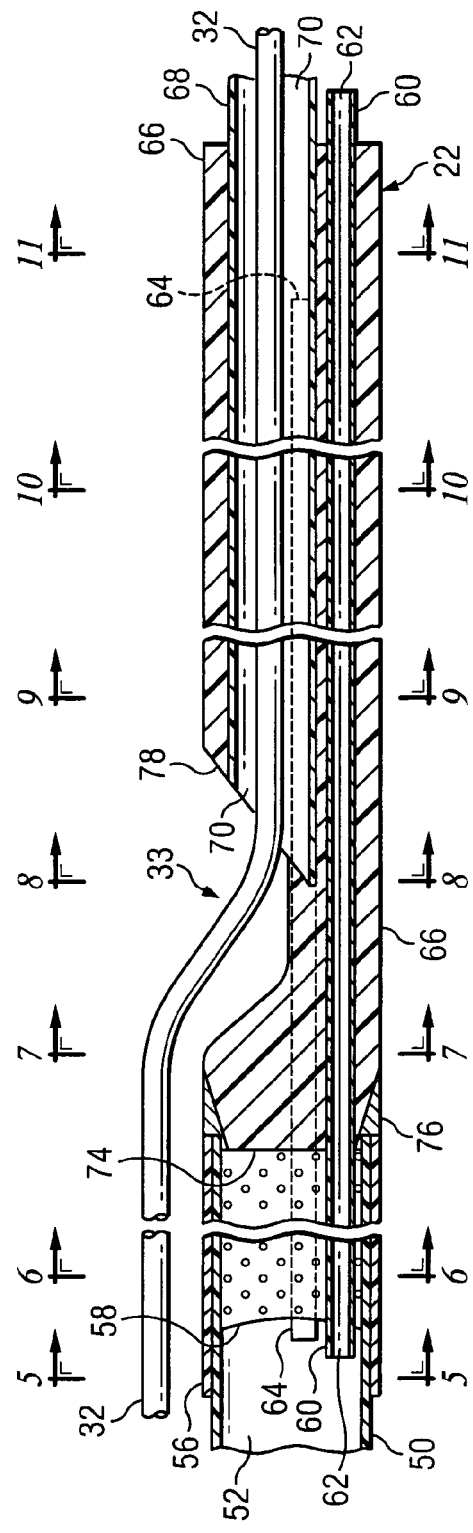

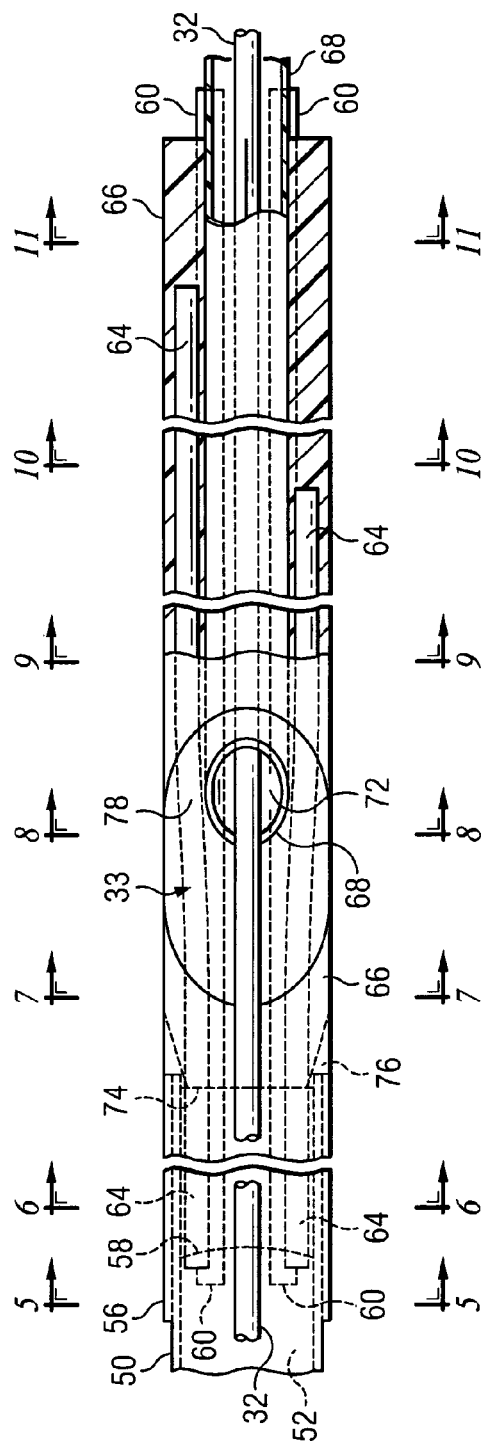
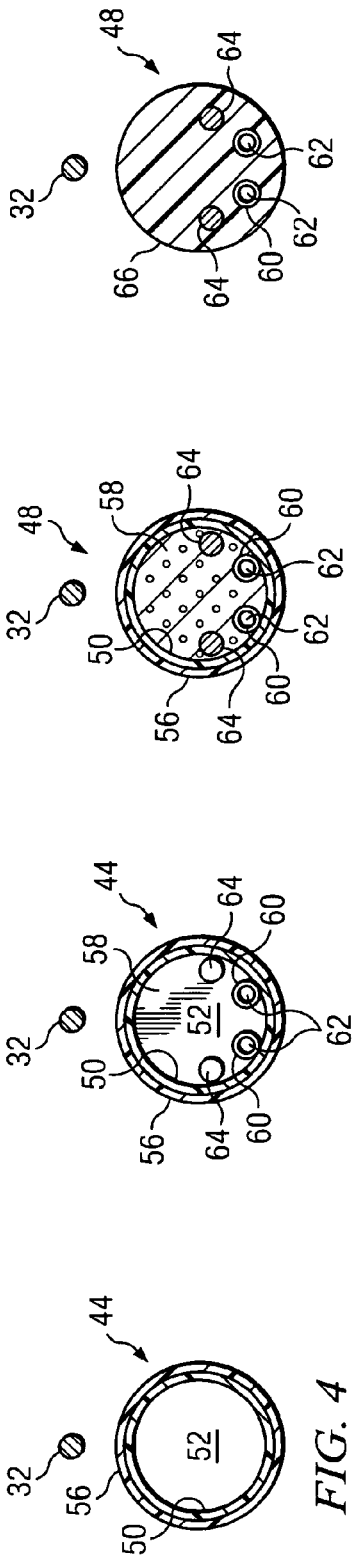
FIG. 3
FIG. 7
FIG. 6
FIG. 5
FIG. 4

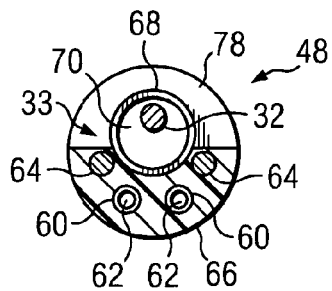
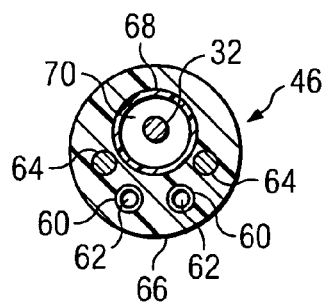
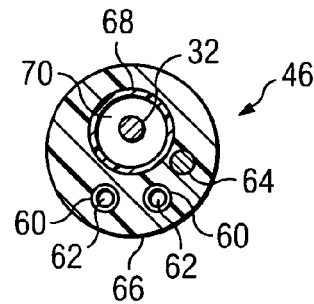
FIG. 8    FIG. 9    FIG. 10
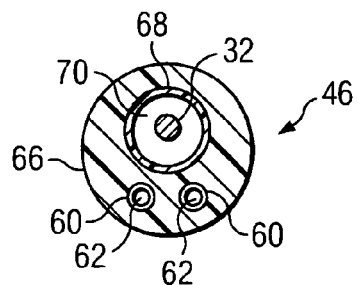
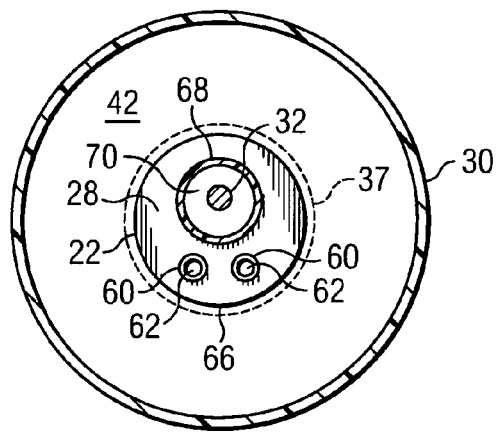
FIG. 11    FIG. 12
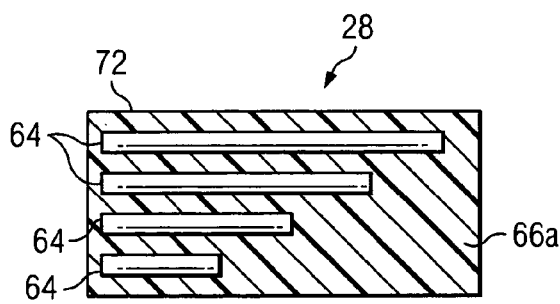
FIG. 13a
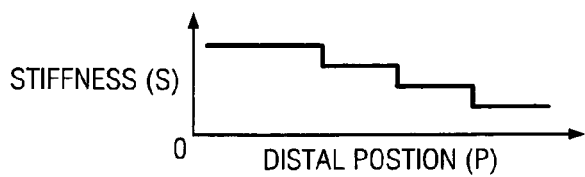
FIG. 13b

RAPID EXCHANGE BALLOON DILATION CATHETER HAVING REINFORCED MULTI-LUMEN DISTAL PORTION

CROSS-REFERENCE TO RELATED APPLICATIONS

This application is a continuation of U.S. patent application Ser. No. 11/174,676, filed Jul. 5, 2005, now U.S. Pat. No. 7,544,201, issued Jun. 9, 2009, and entitled RAPID EXCHANGE BALLOON DILATION CATHETER HAVING REINFORCED MULTI-LUMEN DISTAL PORTION, the specification of which is incorporated herein by reference in its entirety.

TECHNICAL FIELD

The current invention relates generally to angioplasty apparatus, and more specifically to balloon dilation catheters. In particular, it relates to a rapid exchange-type balloon dilation catheter having a distal end that comprises multiple lumens and additional structural reinforcements.

BACKGROUND

As treatment using balloon dilation catheters, for example, Percutaneous Transluminal Angioplasty Catheters (i.e., "PTACs"), has progressed into narrower and more remote vessels within the body, this has necessitated the use of catheters having correspondingly smaller shaft diameters and longer shaft lengths. However, this migration towards catheters with smaller diameter, longer shafts has produced several new problems of its own. First, catheter inflation/deflation time performance (i.e., the time required for inflation and deflation of the balloon) has tended to increase in the longer, smaller diameter catheters as frictional resistance to movement of the inflation fluid through the balloon inflation/deflation lumens of the catheter becomes significant. Second, accessing increasingly smaller body lumens requires that the distal portion of the catheter shaft have sufficient lateral (i.e., side-to-side) flexibility to follow the guidewire as it twists and turns through the smaller, more arduous pathways in the body. If the distal end of the catheter is not flexible enough, it may pull the guidewire out of position in the target lumen rather than follow it. The flexibility of the distal portion of the catheter is often referred to as the "trackability" of the catheter.

In a rapid-exchange type catheter, the guidewire does not run through the entire length of the catheter shaft, but rather runs parallel to the shaft for the majority of it's length, then enters the shaft through a side aperture and runs through only the distal portion of the shaft and the dilation balloon. The side aperture region has a reduced cross section that tends to be a weak point in the structure, and reinforcement in this area is often required. However, the reinforcement necessary to support the side aperture area tends to make the distal portion of the shaft so stiff that it has insufficient trackability.

A need therefore exists, for a rapid exchange balloon dilation catheter (and shaft therefor) with improved trackability in the distal portion. Preferably, the trackability will increase toward the distal end of the shaft.

SUMMARY

The present invention disclosed and claimed herein comprises, in one aspect thereof, a rapid exchange balloon dilation catheter adapted to be utilized with a guidewire. The catheter comprises an elongated catheter shaft having a shaft proximal portion, a shaft distal portion, and a shaft transitional portion disposed therebetween. Each of the proximal, distal and transitional shaft portions has a proximal end and a distal end. A balloon having a proximal end, a distal end and an interior is attached at its proximal end to the distal end of the shaft distal portion. The catheter shaft includes a proximal tubular member having a bore and extending from the proximal end of the shaft proximal portion into the shaft transitional portion. The proximal portion of the bore defines a proximal inflation/deflation lumen for conveying fluids therethrough, and the distal portion of the bore is filled with a fluid-impervious barrier. A distal body extends from the fluid-impervious barrier to the distal end of the shaft distal portion. A plurality of distal tubular members are provided, each having a bore and extending from the proximal inflation/deflation lumen through the fluid-impervious barrier and the distal body to the distal end of the shaft distal portion. The bores of the distal tubular members define distal inflation/deflation lumens for conveying fluids therethrough, the distal inflation/deflation lumens being in fluid communication with the proximal inflation/deflation lumen at their proximal ends and with the interior of the balloon at their distal ends. A guidewire tubular member is provided, having a bore and originating from a side aperture formed in the distal body, extending through the distal body alongside the distal tubular members in a multi-lumen arrangement, then through the interior of the balloon to the distal end of the balloon. The bore of the guidewire tubular member defines a guidewire lumen for conveying a guidewire through the shaft distal portion and the balloon. A plurality of stiffening members are provided, each stiffening member extending from within the fluid-impervious barrier and into the distal body to a respective point within the shaft distal portion.

The present invention disclosed and claimed herein comprises, in another aspect thereof, a shaft for a rapid exchange balloon dilation catheter to be utilized with a guidewire. The shaft comprises a shaft proximal portion, a shaft distal portion, and a shaft transitional portion disposed therebetween. Each of the proximal, distal and transitional shaft portions has a proximal end and a distal end. A proximal tubular member has a bore and extending from the proximal end of the shaft proximal portion into the shaft transitional portion, the proximal portion of the bore defining a proximal inflation/deflation lumen for conveying fluids therethrough and the distal portion of the bore being filled with a fluid-impervious barrier. A distal body extends from the fluid-impervious barrier to the distal end of the shaft distal portion. A plurality of distal tubular members are provided, each distal tubular member having a bore and extending from the proximal inflation/deflation lumen through the fluid-impervious barrier and the distal body to the distal end of the shaft distal portion. The bores of the distal tubular members define distal inflation/deflation lumens for conveying fluids therethrough, the distal inflation/deflation lumens being in fluid communication with the proximal inflation/deflation lumen at their proximal ends and having a fluid passage at their distal ends for conveying fluids out of the distal end of the shaft distal portion. A guidewire tubular member is provided having a bore and originating from a side aperture formed in the distal body, extending through the distal body alongside the distal tubular members in a multi-lumen arrangement, then extending beyond the distal end of the distal body. The bore of the guidewire tubular member defines a guidewire lumen for conveying a guidewire through the shaft distal portion. A plurality of stiffening members is provided, each stiffening member extending from within the fluid-impervious barrier and into the distal body to a respective point within the shaft distal portion.

The present invention disclosed and claimed herein comprises, in a further aspect thereof, a shaft for a balloon dilation catheter to be utilized with a guidewire. The shaft comprises a shaft proximal portion including a proximal tubular member having a bore defining a proximal inflation/deflation lumen. A shaft transitional portion is connected to a distal end of the shaft proximal portion and includes a plurality of distal tubular members and a plurality of stiffening members. The proximal ends of the distal tubular members and the stiffening members are attached to an inner distal surface of the proximal tubular member by a fluid-impervious barrier. Each distal tubular member has a bore defining a distal inflation/deflation lumen, and a proximal end of each distal inflation/deflation lumen is in fluid communication with a distal end of the proximal inflation/deflation lumen. A shaft distal portion is connected to a distal end of the shaft transitional portion and includes a distal body and a guidewire tubular member. The distal body encases the guidewire tubular member and portions of the distal tubing members and the stiffening members, which run alongside one another through the distal body in a multi-lumen arrangement. The guidewire tubular member has a bore and extends from a side aperture formed in the distal body to beyond the end of the distal body. The bore of the guidewire tubular member defines a guidewire lumen for conveying a guidewire therethrough. The distal tubing members extend to the distal end of the distal body, the distal ends of the distal inflation/deflation lumens forming fluid outlets. The stiffening members extend to points disposed between the side aperture and the distal end of the distal body.

BRIEF DESCRIPTION OF THE DRAWINGS

For a more complete understanding, reference is now made to the following description taken in conjunction with the accompanying Drawings in which:

FIG. 1 is an elevation view with partial cross-section of a rapid-exchange balloon dilation catheter in accordance with a first embodiment and the associated guidewire;

FIG. 2 is an enlarged cross-sectional elevation view of portions of the catheter shaft of FIG. 1;

FIG. 3 is a plan view with partial cross-section of the portions of the catheter shaft of FIG. 2;

FIG. 4 is a cross-sectional end view of the catheter shaft and associated guidewire taken along the line 4-4 of FIG. 1;

FIG. 5 is a cross-sectional end view of the catheter shaft and associated guidewire taken along the line 5-5 of FIGS. 2 and 3;

FIG. 6 is a cross-sectional end view of the catheter shaft and associated guidewire taken along the line 6-6 of FIGS. 2 and 3;

FIG. 7 is a cross-sectional end view of the catheter shaft and associated guidewire taken along the line 7-7 of FIGS. 2 and 3;

FIG. 8 is a cross-sectional end view of the catheter shaft and associated guidewire taken along the line 8-8 of FIGS. 1, 2 and 3;

FIG. 9 is a cross-sectional end view of the catheter shaft and associated guidewire taken along the line 9-9 of FIGS. 1, 2 and 3;

FIG. 10 is a cross-sectional end view of the catheter shaft and associated guidewire taken along the line 10-10 of FIGS. 1, 2 and 3;

FIG. 11 is a cross-sectional end view of the catheter shaft and associated guidewire taken along the line 11-11 of FIGS. 1, 2 and 3;

FIG. 12 is a cross-sectional end view through the balloon portion of the catheter taken along the line 12-12 of FIG. 1;

FIG. 13a is a simplified diagram of a catheter distal body with embedded stiffening members in accordance with another embodiment;

FIG. 13b is a graph of stiffness versus distal position for the distal body with embedded stiffening members of FIG. 13a;

FIG. 14b is a graph of stiffness versus distal position for the distal body with embedded stiffening members of FIG. 14a;

FIG. 15b is a graph of stiffness versus distal position for the distal body with embedded stiffening members of FIG. 15a.

DETAILED DESCRIPTION

Figure 14A:
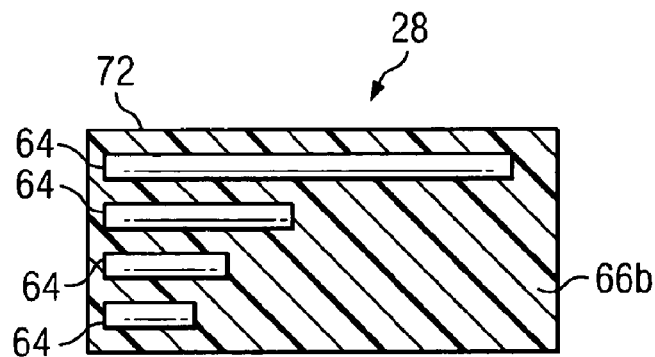
FIG. 14a is a simplified diagram of a catheter distal body with embedded stiffening members in accordance with yet another embodiment.

The current invention is described below in greater detail with reference to certain preferred embodiments illustrated in the accompanying drawings.

Referring now to FIG. 1, there is illustrated a balloon dilation catheter in accordance with one embodiment of the current invention. While this design may be used to make catheters of any diameter, it is particularly suitable for small diameter catheters, e.g., those having a diameter of 5 French or smaller. The catheter 20 includes a shaft 22 having a proximal end 24 that may be affixed to an inflation fitting 26 and a distal end 28 that may be affixed to a dilation balloon 30. As explained in further detail below, a plurality of tubular members comprising the catheter 20 define a plurality of internal passageways, known as lumens. One such tubular member, the guidewire tubular member, extends longitudinally through a portion of the catheter shaft 22. The guidewire tubular member has a bore defining a guidewire lumen that allows a conventional guidewire 32 to be threaded through the corresponding portion of the catheter shaft 22. However, unlike conventional guidewire catheters, wherein the guidewire tubular member extends through the entire shaft 22 from the proximal end 24 to the distal ends 28, the current invention has a so-called "rapid exchange" design wherein the guidewire lumen extends through only the distal portion of the shaft 22, and then exits from the shaft through a side aperture 33 disposed somewhere between the distal end 28 and proximal end 24 of the shaft. A guidewire manipulator or "torquer" 34 may be secured to the guidewire 32 for rotating the guidewire from the proximal end of the catheter. Other tubular members within the catheter shaft 22 define inflation/deflation lumens that convey contrast liquid or other non-compressible inflation fluids through the shaft to and from the balloon, thereby allowing the balloon to be selectively inflated and deflated. The access fitting 26 may be of conventional design, having a fluid port 36 in fluid communication with the shaft's inflation/deflation lumens.

The dilation balloon 30 may be of conventional construction and is typically formed of a relatively non-distensible plastic or polymer material. The envelope of the balloon may be plain, or it may be reinforced with longitudinal, circumferential and/or helical filaments or other reinforcing members. For purposes of illustration, the balloon 30 is shown in its inflated configuration in FIG. 1, however, it will be appreciated that the deflated balloon can typically be folded in such a manner as to have an outside diameter that is approximately the same as that of the catheter shaft 22. It will further be appreciated that the length and diameter of the balloon 30 may vary significantly from that illustrated in FIG. 1 without departing from the scope of the current invention.

The balloon 30 may be attached to the distal end 28 of the catheter shaft 22 using various techniques and configurations known in the art. In the embodiment shown in FIG. 1, an epoxy adhesive is used to connect the proximal end 37 of the balloon directly to the exterior surfaces of the guidewire tubular member 38 and the inflation/deflation lumens where they extend from the end of the catheter shaft. This allows the proximal end 37 of the balloon to butt up against the distal end 28 of the shaft as shown. It will be understood that the lumens are typically protected (e.g., with removable mandrels) during the joining procedure to ensure that adhesive does not block the lumen openings. The distal end 31 of the balloon is connected with a fluid tight seal to the outside (i.e., radial) surface of the guidewire tubular member 38, which extends beyond the distal end of the catheter shaft and passes through the interior of the balloon 30 as shown. The distal end 40 of the guidewire 32 can be seen exiting from the distal end of the guidewire tubular member 38, which typically marks the distal end of the catheter. The inflation/deflation lumens of the catheter, as described in greater detail below, empty from the distal ends 28 of the catheter shaft 22 into the balloon interior 42, thereby allowing inflation and deflation of the balloon 30 by selectively introducing and withdrawing fluid through the fluid port 36 of the access fitting 26.

In order to achieve both high inflation/deflation time performance and high distal flexibility (and hence trackability) the catheter 20 of the current invention has a shaft 22 including a shaft proximal portion 44 having a single lumen configuration disposed toward the proximal end 24 of the shaft, a shaft distal portion 46 having a multi-lumen configuration disposed toward the distal end 28 of the shaft, and a shaft transitional portion 48 disposed therebetween. Typically, the shaft proximal portion 44 constitutes a majority of the catheter shaft's overall length, while the shaft distal portion 46 constitutes a minority of the catheter shaft's overall length.

The shaft proximal portion 44 has a proximal end at the proximal end 24 of the shaft and a distal end abutting the proximal end of the shaft transitional portion 48. The shaft proximal portion 44 includes a single inflation/deflation lumen, but does not include an internal guidewire lumen. The shaft distal portion 46 has a proximal end abutting the distal end of the shaft transitional portion 48 and a distal end at the distal end 28 of the shaft. The shaft distal portion 46 includes an internal guidewire lumen and a plurality of inflation/deflation lumens running parallel to, but separate from, the guidewire lumen. The shaft transitional portion 48 is disposed between the shaft proximal portion 44 and the shaft distal portion 46 as just described. The internal configuration of the catheter shaft 22 transitions from the single lumen configuration of the shaft proximal portion 44 to the multi-lumen configuration of the shaft distal portion 46. The side aperture 33 for insertion of the guidewire 32 into the distal portion of the shaft is disposed within this transitional portion.

As described in further detail below, the distal portion 46 of the shaft exhibits progressive increasing flexibility between side aperture 33 and the distal end 28. In other words, the flexibility of the distal portion 46 of the shaft becomes progressively greater (i.e., it is easier to bend) as the distance from the side aperture 33 increases. This progressive distal flexibility allows the distal portion 46 of the catheter shaft 22 to be relatively flexible near the balloon 30 for maximum trackability and relatively stiff near the side aperture 33 to prevent excessive bending at the point of reduced cross-section. The progressive distal flexibility may be exhibited as a continuous reduction in the stiffness of the shaft, or as a series of step-wise reductions in the stiffness of the shaft. At a minimum, there will be at least one change in the stiffness of the distal portion of the shaft, and preferably two or more changes in stiffness of the distal portion of the shaft between the side aperture 33 and the distal end 28.

Referring now to FIGS. 2 and 3, there are illustrated, respectively, a cross-sectional side view and a partial cross-sectional elevation view of the catheter shaft 22 centered on the transitional portion 48. It will be appreciated that for purposes of illustration, selected portions of the shaft 22 having a constant cross-section have been omitted (as indicated by the broken end lines), thus the actual length of the shaft and/or portions thereof, may be greater than that shown in the figures.

Referring now to FIG. 4, there is illustrated a lateral cross-section of the proximal portion 44 of the shaft, i.e., the single lumen portion. It will be appreciated that, for purposes of illustration, the wall thicknesses of the various tubular members may not be shown to scale in FIGS. 1-12, and the spacings between the various tubular members and around the guidewire may be exaggerated for clarity. The shaft proximal portion 44 includes a proximal tubular member 50 having a bore 52 that serves as the proximal inflation/deflation lumen. As previously described, the proximal inflation/deflation lumen 52 is in fluid communication with the fluid port 36 of the access fitting 26, allowing the catheter shaft to transport inflation fluid for inflating the balloon 30. Accordingly, the proximal tubular member 50 must be strong enough to withstand the balloon's maximum inflation pressure without bursting. As in other rapid exchange catheters, the guidewire 32 is not conveyed through the proximal portion 44 of the catheter shaft, but rather is disposed externally as shown.

The proximal tubular member 50 of the shaft proximal portion 44 may be formed of suitable materials such as plastic, elastomers, metal or metal alloy. For some catheters, the proximal tubular member 50 may be formed of Nylon-11 or of polyether block amide (PEBA) thermoplastic elastomer, such as that sold under the trademark Pebax®. In some cases, the Nylon-11 or PEBA elastomer may be loaded with approximately 20% bismuth by weight to provide partial radiopacity. For other catheters, especially for small diameter catheters, e.g., those having an outside diameter of about 5 French or smaller, it is preferred to use higher strength materials for the proximal tubular member 50 in order to keep the wall thickness as low as possible, and also to provide adequate torsional stiffness to the overall shaft 22. Thus, in preferred embodiments, the proximal tubular member 50 is made of polyamide plastic, which is significantly stiffer than either Nylon-11 or PEBA.

The proximal tubular member 50 may be sheathed in a jacket 56 made of a different material. Typically, the jacket 56 is not used to provide additional structural strength, but rather to change certain characteristics of the shaft proximal portion 44 (i.e., as compared to the characteristics of the proximal tubular member 50 alone). For example, ordinary polyamide plastic is relatively radio-transparent, and not easily loaded with radiopacifiers. Thus, where tubular member 50 is made of polyamide plastic, the jacket 56 may be made of the radio-paque material to make the proximal portion 44 of the catheter shaft more visible by radiography. In other examples, the proximal jacket 56 may be made of a material that provides a smooth exterior surface that minimizes the tendency for blood cells to accumulate thereupon and/or of a hydrophilic material that exhibits lubricity when it comes into contact with blood. The jacket 56 may be extruded or co-extruded around the proximal tubular member 50 during its manufacture, or it may be bonded to the proximal tubular member by thermal-compression molding or similar processes at a later time. In a preferred embodiment, the proximal portion jacket 56 is formed of a polyether block amide (PEBA) thermal plastic elastomer such as that sold under the trademark Pebax®. PEBA elastomer such as Pebax® brand PEBA may be readily loaded with radiopacifiers, e.g., bismuth, and are available in plasticizer and additive-free medical grade. Thus, in another preferred embodiment, the proximal tubular member 50 is made of a polyamide plastic and the proximal portion jacket 56 is made of Pebax® brand grade 7233 PEBA loaded with approximately 20% (by weight) bismuth.

Referring again to FIGS. 2 and 3, and now also to FIGS. 5-11, further details of the configuration of the shaft 22 are shown. As previously described, the proximal portion 44 of the shaft has a single lumen configuration including a proximal tubular member 50, the bore of which defines a proximal inflation/deflation lumen 52 and may further include a jacket 56 sheathing the exterior surface of the proximal tubular member. The proximal tubular member 50, and jacket 56 (if present) extend past the distal end of the shaft proximal portion 44 and form part of the shaft transitional portion 48. However, in the shaft transitional portion, the bore 52 of the proximal tubular member 50 is filled with a fluid-impervious barrier 58, effectively terminating the proximal inflation/deflation lumen 52. Extending through the fluid barrier 58 are a plurality of distal tubular members 60, each of which has a bore 62 defining a distal inflation/deflation lumen that is in fluid communication with the proximal inflation/deflation lumen 52. Also extending at least into, if not through, the fluid barrier 58 is at least one stiffening member 64.

The shaft transitional portion 48 further includes a portion of a distal body 66 disposed distally adjacent to the fluid barrier 58. The distal body 66 may extend somewhat into the distal end of the proximal tubular member 50, however, this is not required. The distal body 66 extends (in the distal direction) through the rest of the shaft transitional portion 48 and into the shaft distal portion 46. Embedded within the distal body 66 is a guidewire tubular member 68 having a bore 70 defining a guidewire lumen for slidingly receiving the guidewire 32. The proximal end of the guidewire tubular member 68 is typically disposed a short distance from the fluid barrier 58, and may be cut at a slant or otherwise shaped to facilitate entry of the guidewire 32 into the guidewire lumen 70. The distal body 66 is cut back or molded to have a reduced cross-section at the proximal end of the guidewire tubular member 68, thereby forming the side aperture 33 that allows passage of the guidewire to and from the guidewire lumen 70.

Extending through the distal body 66 below the reduced cross-section area of the side aperture 33 are the distal tubular members 60 and stiffening members 64. The distal tubular members 60 allow inflation fluid to continue traveling from the proximal end 24 of the catheter shaft 22 toward the distal end 28. The stiffening members 64 provide structural support to the distal body 66 in the region of reduced cross-section at the side aperture 33, preventing the shaft from being so weak that it buckles or otherwise fails during normal handling or use.

The distal portion 46 of the shaft is disposed distally adjacent to the shaft transitional portion 48, and extends to the distal end 28, where it is adapted for connection to the proximal end 37 of the balloon 30. The proximal end of the shaft distal portion 46 may be considered to be the first cross-sectional plane where the full guidewire tubular member 68, distal tubular member 60 and stiffening member 64 are all present, however, this is somewhat arbitrary and has no particular effect on the scope of the invention. It is significant, however, that the shaft distal portion has progressive distal flexibility, i.e., the distal portion of the shaft becomes more flexible (i.e., less stiff) as it gets closer to the distal ends 28.

In the embodiment shown in FIGS. 2 and 3, the progressive distal flexibility of the shaft distal portion 46 results from the staggered termination of multiple stiffening members 64. As best seen in FIG. 3, the two stiffening members 64 are terminated at different points between the side aperture 33 and the distal end 28. Since the guidewire tubular member 68 and distal tubular members 60 extend continuously through the shaft distal portion 46, the shaft will get more flexible (i.e., less stiff) at the point each stiffening member 68 is discontinued. For example, at the plane of the cross-section of FIG. 9, two stiffening members 64 are present, and the shaft will have relatively high stiffness/low flexibility. Moving distally to the plane of the cross-section of FIG. 10, one of the stiffening members has been discontinued, thus only one stiffening member is present. Accordingly, the shaft at this point will be less stiff/more flexible than it was at the previous cross-section. Moving distally still further to the plane of the cross-section of FIG. 11, both stiffening members 64 have now been discontinued, and no stiffening members are present. Accordingly, the shaft at this point will be even less stiff/more flexible than it was at the previous cross-section. This is only one example of progressive distal flexibility, and it will be appreciated that many other configurations may be used. For example, by changing the number of the stiffness members, and/or the spacing between their terminations, the progressive flexibility of the distal portion of the shaft may be tailored as desired, e.g., the flexibility may increase linearly with distal position in one example and have a nonlinear relation to distal position in another example.

Referring now to FIGS. 13a, 13b, 14a, 14b, 15a and 15b, there are illustrated examples of alternative configurations for providing progressive distal flexibility in additional embodiments. FIG. 13a shows a simplified representation of the distal body 66a between an intermediate point 72 and the distal end of the shaft 28. Embedded within the distal body 66a are four stiffening members 64 of equal constant cross-section, but having different lengths varying according to a linear relationship. If the stiffening members 64 are aligned at the proximal end, this arrangement will produce a distal body 66a having a step-wise decreasing stiffness (S) that has a generally linear relationship with distal position (P), as shown in FIG. 13b. It will be appreciated that flexibility is inversely proportional to stiffness. Thus, the distal body 66a will exhibit distally progressive flexibility having a generally linear nature.

Figure 14B:
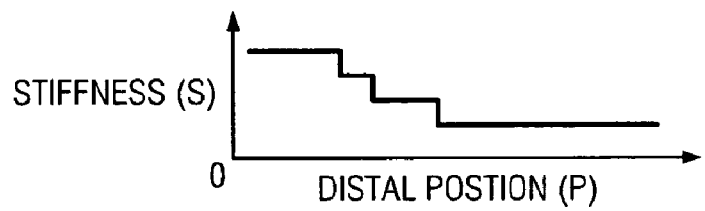

FIG. 14a shows a simplified representation of a distal body 66b having embedded there within four stiffening members 64 of equal cross-section area but having the different lengths varying according to a nonlinear relationship. If the stiffening members 64 are aligned at the proximal end 72, this arrangement will produce a distal body 66b having a step-wise decreasing stiffness (S) that has a generally nonlinear relationship with distal position (P), as shown in FIG. 14b.

Figure 15A:
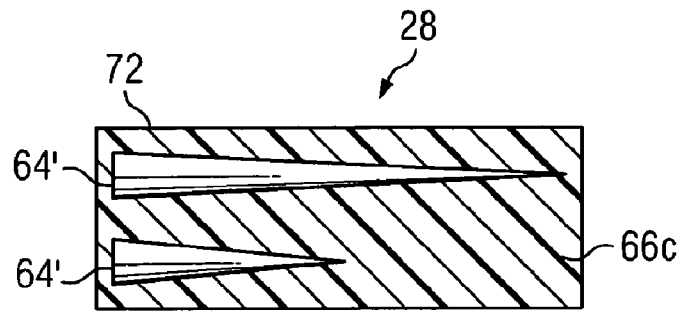
FIG. 15a is a simplified diagram of a catheter distal body with embedded tapered stiffening members in accordance with a further embodiment.
Figure 15B:
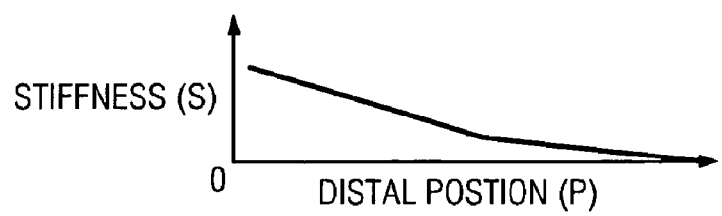

FIG. 15a shows a simplified representation of a distal body 66c similar to those described above. Embedded within the distal body 66c are two stiffening members 64', however, these strengthening members do not have a constant cross-section, but rather have a tapered configuration such as might be obtained by heating and stretching plastic rods or by molding or machining tapered rods. If the stiffening members 64' are aligned at the proximal end 72 the arrangement will produce a distal body 66c having a continuously decreasing stiffness characterized by two linear portions having different slopes as shown in FIG. 15b. In this manner, the flexibility of the distal portion of the catheter shaft 22 may be customized according to particular procedures or to a particular user's preference.

The distal tubular members 60 may be formed of suitable materials such as plastic, elastomers, metal or metal alloy. For small diameter catheters, it is preferred to use high strength materials for the distal tubular members in order to keep their wall thicknesses as low as possible, and also to provide adequate torsional stiffness to the shaft distal portion 46. In preferred embodiments, the distal tubular members 60 are made of polyamide plastic. The guidewire tubular member 68 may also be formed of suitable material such as plastic, elastomers, metal or metal alloy. Among the plastics suitable for use are Nylon, including Nylon-11, and polyamide plastic. For small diameter catheters, e.g., those having an outside diameter of about 5 French or smaller, it is preferred to use higher strength materials such as polyamide in order to keep the wall thickness as low as possible and thereby maximize the cross-sectional area available for the guidewire lumen 70 and the distal inflation/deflation lumens 62. Thus, in preferred embodiments, both the guidewire tubular member 38 and the distal tubular members 60 will be made of polyamide plastic.

The stiffening members 64 may be made of suitable materials such as plastic, elastomers, metal or metal alloys. Although the stiffening members 64 may be tubular, this is not required since the stiffening members do not incorporate the lumen. Thus, the stiffening members 64 may be shaped as tubes, rods, plates, channels or other structural shapes. The stiffening members may be of constant cross-section, such as extrusions, or they may be tapered (see FIG. 15a) or have other variable cross-sections. In a preferred embodiment, the stiffening members 64 are made of polyetheretherketone (PEEK) thermoplastic. PEEK has a natural tensile strength of approximately 13,000-14,000 PSI, and may be filled with glass fibers or carbon fibers to yield higher tensile strengths, e.g., approximately 22,500 PSI for 30% glass file and approximately 30,000 PSI for 30% carbon fiber fill.

As previously described, the fluid barrier 58 serves to block the proximal inflation/deflation lumen 52, thereby forcing the inflation fluid to flow through the distal inflation/deflation lumen 62 to reach the balloon 30. However, the fluid barrier 58 also serves to anchor the transitional portion 48 and distal portion 46 of the shaft to the proximal portion 44 by bonding the exterior surfaces of the distal tubing members 60 and stiffening members 64 to the interior surfaces of the proximal tubing member 50. Various conventional bonding agents such as glues, epoxies and the like may be used with the fluid barrier 58, provided the material has sufficient fluid resistance, adhesive strength and mechanical strength to resist the maximum balloon inflation pressure and the mechanical forces exerted on the catheter during handling and use. In a preferred embodiment, a two part medical grade epoxy is used for the fluid barrier 58.

In a preferred embodiment, the distal body 66 is formed of a plastic or elastomer material that can be molded around the tubular members 60 and 68 and the stiffening member 64 by thermal-compression molding, i.e., using pressure and heat. In one embodiment, the distal body 66 is formed of a polyether block amide (PEBA) thermal plastic elastomer, such as Pebax® brand PEBA. PEBA thermal plastics may be molded using pressure and heat. Since flexibility is desirable for the shaft distal portion 46, using a relatively soft PEBA formulation for the distal body 66 appears to have advantages. If radiopacity is required, the distal body 66 may be made of a radiopaque material or filled with a radiopaque material such as bismuth. In a preferred embodiment, the distal body 66 is made of a Pebax® brand grade 4033 PEBA. In a more preferred embodiment, the distal body is made of PEBA filled with approximately 20% (by weight) bismuth.

As best seen in FIG. 2, in some embodiments, the proximal end 74 of the distal body 66 may be tapered to fit into the extreme distal end of the proximal tubular member 50 (e.g., to assist in aligning the two portions during assembly). Since it is preferable that the outside diameter of the catheter shaft 22 be as smooth as possible, a filler band 76 may be added to the shaft after connection of the shaft transitional portion 48 to the shaft proximal portion 44. The filler band 76 may be made of a suitable material that is compatible with the adjacent proximal jacket 56 and distal body 66. The material of the filler band 76 may be the same as that of the jacket 56 for the distal body 66, or it may be a different material altogether. Preferably, the material of the filler band 76 will be a plastic or elastomer material that can be molded around the perimeter of the assembled catheter shaft 22 using pressure and heat (e.g., thermal compression molding). In one preferred embodiment, the filler band 76 is formed of a polyether block amide (PEBA) thermal plastic elastomer such as Pebax® brand PEBA.

Referring now to FIG. 5, there is illustrated a cross-section of the catheter shaft 22 taken near the distal end of the shaft proximal portion 44. The configuration of the shaft is essentially the same as that shown in FIG. 4, including the proximal tubular member 50 and the jacket 56. The proximal inflation/deflation lumen 52 defined by the bore of the proximal tubular member 50 is present at the point of the cross-section, however, the barrier 58 is physical nearby in the distal direction. The proximal ends of the distal tubular member 60 and stiffening members 64 are also visible extending from the nearby end of the barrier 58. The distal inflation/deflation lumens 62 are seen opening into the proximal inflation/deflation lumen 52 such that there is fluid communication between them. The guidewire 32 remains outside the catheter shaft at this point.

Referring now to FIG. 6, there is illustrated a cross-section of the catheter shaft 22 taken near the proximal end of the transitional portion 48. The proximal tubular member 50 and proximal jacket 56 are still present, however, the proximal inflation/deflation lumen is no longer present, its place having been taken by the barrier 58. The distal tubular member 60 and stiffening members 64 extend through the barrier 58. It will be appreciated that the barrier 58 bonds the distal tubular member 60 and stiffening members 64 to the interior of the proximal tubular member 50, thereby securing the transitional and distal portions of the shaft to the proximal portion. The guidewire 32 remains outside the catheter shaft at this point.

Referring now to FIG. 7, there is illustrated a cross-section of the catheter shaft 22 taken through an intermediate part of the transitional portion 48. At this point, the distal body 66 has replaced the proximal tubular member 50, the jacket 56 and the barrier 58. The distal tubular members 60 and the stiffening members 64 are embedded in the distal body 66, serving to anchor the distal body to the proximal portions of the catheter shaft. The distal inflation/deflation lumens 62 allow inflation fluid to be conveyed through the shaft toward the balloon 30. The guidewire 32 remains outside the catheter shaft at this point.

Referring now to FIG. 8, there is illustrated a cross-section of the catheter shaft 22 taken near the distal end of the transitional portion 48. At this point, the distal body 66 has a reduced cross-section due to the presence of the side aperture 33. Nearby in the distal direction, the proximal end of the guidewire tubular member 68 can be seen entering the distal body 66 through the distal wall 78 of the side aperture. The guidewire 32 can also be seen entering the guidewire lumen 70 defined by the bore of the guidewire tubular member 68. The distal tubular members 60 and the stiffening members 64 are embedded in the remaining portion of the distal body 66. The distal inflation/deflation lumen 62 allows inflation fluid to be conveyed through the shaft toward the balloon 30. The stiffening members 64 provide reinforcement of the catheter shaft 22 at the point of reduced cross-section necessitated by the presence of the side aperture 33. If the stiffening members 64 were not present, then either the shaft would be subject to excessive bending and possible failure at the side aperture 33, or alternatively, the distal tubular members 60 would have to be much stiffer (e.g., thicker walls and/or stronger material), which would not be conducive to providing the necessary flexibility that is needed at the distal end of the catheter shaft near the balloon 30.

Referring now to FIGS. 9-11, there are illustrated successive cross-sections of the catheter shaft 22 taken through the shaft distal portion 46 moving from near the proximal end toward the distal end. Referring now specifically to FIG. 9, at this point the distal body 66 has returned to a full-diameter cross-section. Embedded within the distal body 66 are the guidewire tubular members 68 and the distal tubular members 60 with their respective lumens 70 and 62. The guidewire 32 can pass through the guidewire lumen 70 and inflation fluid can pass through the distal inflation/deflation lumens 62. Both stiffening members 64 are also embedded in the distal body, providing high relative stiffness to the shaft at this point. Referring next specifically to FIG. 10, at this point the shaft has substantially the same configuration as in FIG. 9, except that one of the stiffening members 64 is not present, having terminated in the intervening portion of the shaft (see FIG. 3). This results in the catheter shaft having less thickness, i.e., greater flexibility, than it had at the point of the previous cross-section. Referring next specifically to FIG. 11, at this point the shaft has substantially the same configuration as in FIG. 10, except that there are no stiffening members 64 present, the last remaining stiffening member having terminated in the intervening portion of the shaft (again, see FIG. 3). This of course results in the catheter shaft having even less stiffness, i.e., even greater flexibility, than it had at the point of the cross-section of FIG. 10. Thus, the staggered termination of the stiffening member 64 provides the distal portion 46 of the shaft with progressively increasing flexibility toward the distal ends 28.

Referring now to FIG. 12, there is illustrated a representative lateral cross-section of the catheter 20 taken through the inflated dilation balloon 30. The cross-section illustrated in FIG. 12 is taken facing towards the distal end 28 of the catheter shaft 22 and the proximal end 37 of the balloon. The guidewire tubular member 68 and its lumen 70 pass entirely through the balloon 30, however, the distal tubular members 60 terminate near the distal end 28 of the catheter, and their respective distal inflation/deflation lumens 62 are in fluid communication with the balloon interior 42. Thus, the combination of the proximal and distal inflation/deflation lumens 52 and 62 provide a continuous fluid channel through the catheter shaft 22 between the access fitting 26 on the proximal end 24 and the balloon interior 42 on the distal end 28. This allows the balloon 30 to be selectively inflated or deflated via the fluid port 36 of the access fitting 26.

Figure 16A:
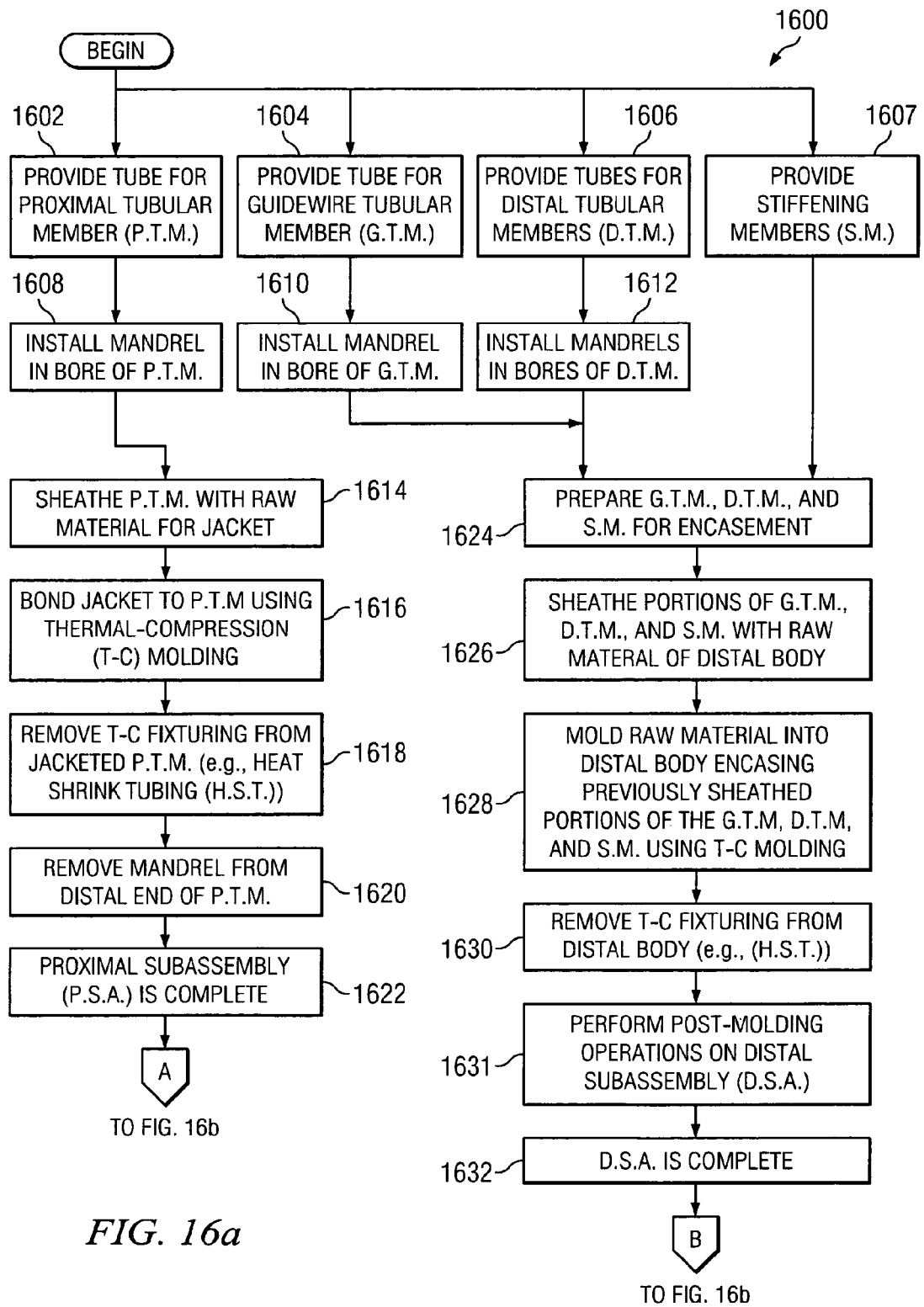
FIGS. 16a and 16b are a flow chart showing a method for manufacturing a hybrid catheter shaft in accordance with another embodiment.
Figure 16B:
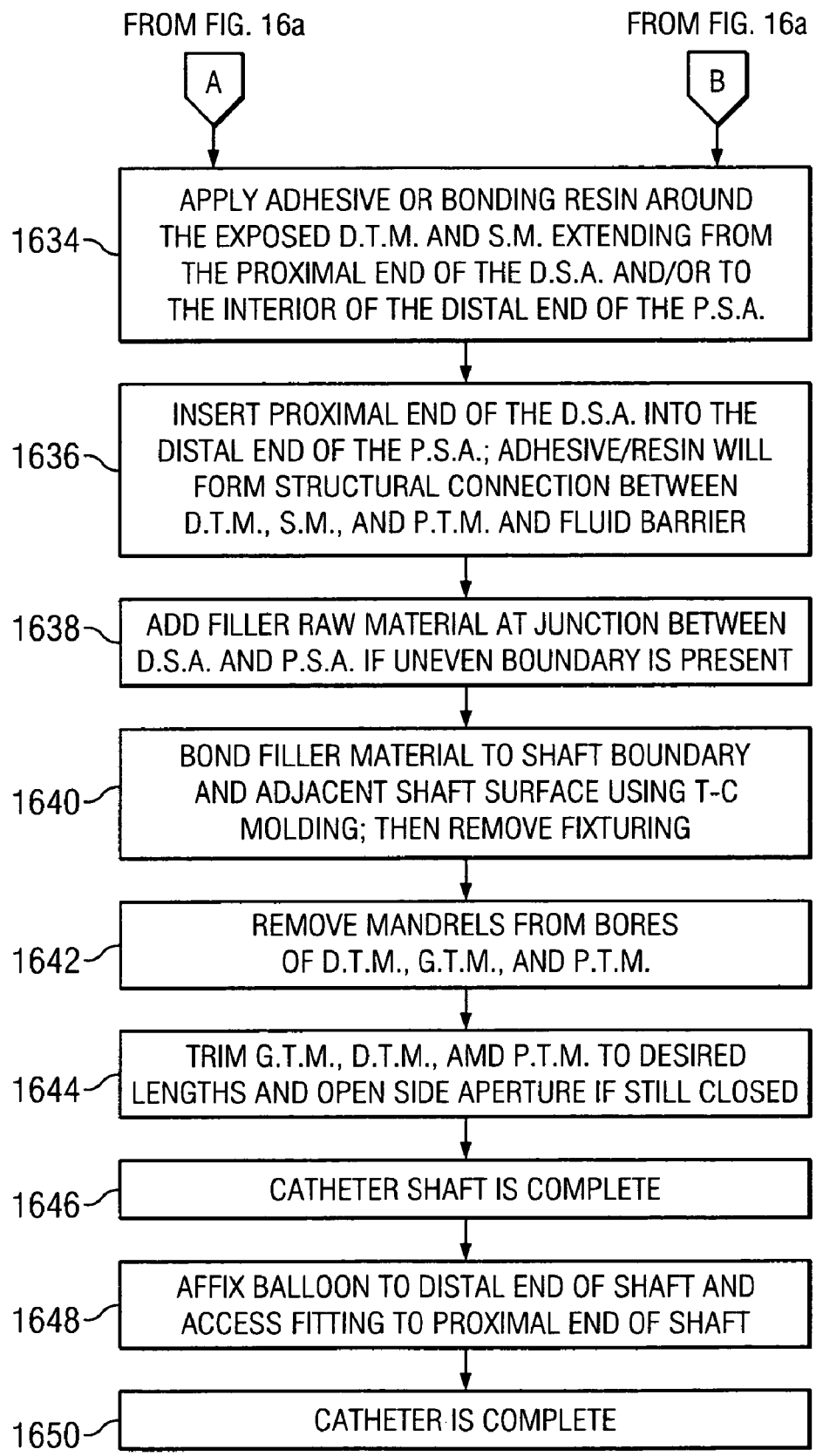

Referring now to FIGS. 16a and 16b, there is illustrated a method for manufacturing a catheter shaft and a balloon dilation catheter in accordance with another embodiment. The method of manufacture 1600 begins with providing tubes for the proximal tubular member, guidewire tubular member and distal tubular member as represented by blocks 1602, 1604 and 1606, respectively. The various tubular members may be made of plastics or other materials as previously described. In preferred embodiments, one or all of the proximal tubular member, guidewire tubular member and distal tubular members are made from polyimide plastic. Next, a mandrel made of steel or other noncompressible material is inserted into the bore of each of the tubes as shown in blocks 1608, 1610 and 1612, respectively. The outer diameter of each mandrel is selected to slip closely within the bore of its respective tubular member, thereby providing support for the walls of the tubular member during subsequent processing steps, and ensuring that unwanted materials do not enter the bores of the tubular members during subsequent processing steps.

In addition, stiffening members are provided as indicated in block 1607. The SM may be made of plastic or other materials as previously described. The SM may be rods, tubes, plates or other shapes as previously described, which may have constant or variable cross sections. In preferred embodiments, the SM are made from PEEK plastic rods having a constant cross section.

As the method 1600 continues, the tubular members and SM may require additional processing. For convenience, the following description will first describe the additional processing of the proximal tubular member to form a proximal subassembly, then the processing of the remaining tubular members and SM. However, it will be appreciated that the order of processing these members may be changed without departing from the scope of the invention. As shown in block 1614, the proximal tubular member is next loosely sheathed with a suitable jacket raw material, e.g., PEBA thermoplastic elastomer. Such jacket material is often supplied in the form of an extruded tube that may be slipped over the proximal tubular member, however, other forms of jacket raw material may be used. Next, as shown in block 1616, the jacket material is bonded to the exterior of the proximal tubular member using thermal compression molding or other known bonding techniques. In thermal compression molding, a combination of heat and pressure causes the molding material to "flow" and adhere to the exterior of the subject member. In a preferred embodiment, the thermal compression molding is accomplished by placing a length of heat-shrink tubing over the previously assembled jacket raw material, proximal tubing member and mandrel, then heating this assembly in an oven. The heat from the oven serves to soften the jacket material so that it may flow, while at the same time the heat causes the heat-shrink tubing to shrink, thereby compressing the softened jacket material tightly against the exterior or the proximal tubular member. The mandrel inside the bore of the proximal tubular member prevents the collapse of the tubing walls even though they are subjected to considerable compression forces during the molding process. The compression molding provided by the heat-shrink tubing when heated is very uniform, thereby avoiding the formation of seam lines or any other surface irregularities on the surface of the jacket that might result from other molding techniques. After the jacket has been bonded to the exterior of the proximal tubular member, the heat-shrink tubing may be removed from the assembly, as indicated in block 1618. Of course, in embodiments which do not include the exterior jacket, the operation shown in blocks 1614, 1616 and 1618 may be omitted. After jacketing, the mandrel may be removed from at least the distal end of the proximal tubular member as shown in block 1620. The proximal tubular member and jacket, if present, may next be cut to their final lengths or otherwise further processed, completing preparation of a proximal subassembly as indicated in block 1622.

The method 1600 for constructing the catheter shaft now continues with further details of the construction of a distal subassembly. First, the guidewire tubular member and distal tubular members, with their respective mandrels installed as shown in blocks 1610 and 1612, and the SM as shown in block 1607, are prepared for encasement in the distal body of the shaft, as shown in block 1624. This preparation may include cutting the members to predetermined lengths and arranging them in predetermined configuration for assembly. Typically, the members will be arranged so that the distal end of the guidewire tubular member extends past the distal tubular members and SM in the distal direction, the proximal ends of the distal tubular members and SM extend past the guidewire tubular member in the proximal direction, and the SM terminate at staggered points along the guidewire tubular member. Next, as shown in block 1626, portions of the guidewire tubular member, distal tubular members and SM are loosely sheathed with the raw material to be used for the distal body. It is important to note that various portions of the guidewire tubular member, distal tubular members and SM are not sheathed with this material as they will remain unencased by the distal body. In particular, the proximal ends of the distal tubing members and SM will be left unsheathed for connection to the proximal subassembly, and the distal end of the guidewire tubular member will be left unsheathed for later connection to the balloon. In a preferred embodiment, the raw material for the distal body is provided in the form of an extruded plastic tube that can be slipped over portions of the guidewire tubular member, distal tubular members and SM, which are then positioned relative to one another and relative to the raw distal body tube as previously described. In a preferred embodiment, the sheathing material is a PEBA thermoplastic elastomer.

Next, as shown in block 1628, the distal body raw material is molded around the sheathed portions of the guidewire tubular member, distal tubular members and SM using thermal compression molding to form the distal body. As previously described, this thermal compression molding may be accomplished by slipping a length of heat-shrink tubing over the previously assembled guidewire tubular member, distal tubular members, SM and sheathing material, and then heating the entire assembly in an oven. The heat will soften the distal body raw material allowing it to flow between and around the various members under the pressure generated by the contracting heat-shrink tubing. The guidewire tubing member and distal tubing member are protected from collapse during the thermal compression molding by the presence of the mandrels within their respective bores. As previously described, the heat shrink tubing provides exceptionally smooth surface finish on the final molded distal body. After the thermal compression molding is complete, the thermal-compression fixturing (e.g., heat-shrink tubing) may be removed as shown in block 1630. Finally, any required trimming of the exposed ends of the members, tapering of the proximal end of the distal body and other post-molding procedures (block 1631) may be performed to complete the distal subassembly as indicated in block 1632. It will be appreciated that construction of the proximal subassemblies and the distal subassemblies are essentially independent of one another such that it makes no difference which subassembly is completed first in the method 1600.

Once a proximal subassembly and a distal subassembly are available, final assembly may proceed as indicated in block 1634. In final assembly, an adhesive or bonding resin, e.g., a two-part medical grade epoxy, is applied to the distal subassembly around the exposed distal tubular members and SM in the area immediately adjacent to the proximal end of the distal body. Adhesive may also be applied to the interior distal end of the proximal subassembly. Next, as shown in block 1636, the proximal ends of the distal tubing members and SM (of the distal subassembly) are inserted into the bore of the proximal tubular member (of the proximal subassembly) until the adhesive-coated region adjacent to the distal body abuts against the distal end of the proximal subassembly. This adhesive will form the fluid-tight barrier filling the distal part of the proximal inflation/deflation lumen of the shaft, while at the same time providing the structural connection between the proximal subassembly and the distal subassembly. Since the mandrels remain in place within the distal tubular members during the bonding process, no adhesives are able to enter the bores of these tubes and cause an undesired obstruction.

In a preferred embodiment, the proximal end of the distal subassembly may be slightly tapered prior to final assembly to facilitate the centering of the distal subassembly in the open end of the proximal subassembly. In such embodiments, the taper may result in the creation of an undesirable seam, gap or depression on the surface of the shaft at the joint between the proximal subassembly and the distal subassembly. As shown in block 1638, a band of filler material may be added into the gap or depression at the joint between the distal subassembly and the proximal subassembly to smooth the exterior of the shaft. This filler may be bonded (block 1640) through the use of thermal compression molding by first slipping a tube of raw filler material over the uneven region, then slipping a length of heat-shrink tubing over the filler material and surrounding shaft, and then heating it in an oven. As previously explained, the raw filler material will be softened by the heating, and the heat-shrink tubing will then contract to provide pressure molding that bonds the filler material to the shaft surface and eliminates any unevenness in the shaft surface formed during final assembly. This method of assembly will result in the exterior surface of the catheter shaft being very smooth around the junction area.

After all thermal compression molding is completed, the mandrels may be removed from the guidewire tubular member, the distal tubular members and proximal tubular member as indicated in block 1642. Next, any final trimming of the guidewire tubular member and distal tubular members to desired lengths may be performed as shown in block 1644. Further, the side aperture may be cut open to expose the guidewire lumen. This completes construction of the catheter shaft as shown in block 1646. The catheter shafts manufactured using this method may subsequently be attached to dilation balloons and access fittings (block 1648) to manufacture complete catheter assemblies (block 1650), or alternatively, they may be sold as components for use by others in constructing their own catheters. It will be appreciated that while the assembly method 1600 described above is a preferred method of constructing the catheter shafts and catheters previously described in connection with FIGS. 1-12, variations of this method and other methods may also be used for producing the catheter shafts without departing from the scope of the invention.

While the invention has been shown or described in a variety of its forms, it should be apparent to those skilled in the art that it is not limited to these embodiments, but is susceptible to various changes without departing from the scope of the invention.

What is claimed is:

1. A rapid exchange balloon dilation catheter, the catheter comprising:
   a catheter shaft having a proximal end and a distal end;
   a balloon having a proximal end, a distal end and an interior, the proximal end of the balloon being attached to the distal end of the catheter shaft;
   the catheter shaft further including:
      a proximal shaft portion, a distal shaft portion, and a transitional shaft portion disposed therebetween including a fluid impervious barrier;
      a plurality of distal tubular members originating through the fluid-impervious barrier of the transitional shaft portion and extending to the interior of the balloon;
      a guidewire tubular member having a bore originating from a side aperture and extending through the interior of the balloon to the distal end of the balloon; and
      a plurality of stiffening members extending from within the fluid-impervious barrier through the transitional shaft portion and into the distal shaft portion.

2. A catheter in accordance with claim 1, wherein the distal tubular members are formed of one of a plastic, an elastomer, a metal and a metal alloy.

3. A catheter in accordance with claim 2, wherein the distal tubular members are formed of a nylon (polyamide) material.

4. A catheter in accordance with claim 2, wherein the distal tubular members are formed of a polyimide material.

5. A catheter in accordance with claim 1, wherein the guidewire tubular member is formed of one of a plastic, an elastomer, a metal and a metal alloy.

6. A catheter in accordance with claim 5, wherein the guidewire tubular member is formed of a nylon (polyamide) material.

7. A catheter in accordance with claim 5, wherein the guidewire tubular member is formed of a polyimide material.

8. A catheter in accordance with claim 1, wherein the catheter shaft becomes more flexible as it gets closer to the distal end.

9. A catheter in accordance with claim 8, wherein at least one of the stiffening members has a different length from other stiffening members.

10. A catheter in accordance with claim 8, wherein at least one of the stiffening members has a cross section that varies along its length.

11. A shaft for a rapid exchange balloon dilation catheter, the shaft comprising:
    a proximal shaft portion, a distal shaft portion, and a transitional shaft portion disposed therebetween including a fluid impervious barrier;
    a plurality of distal tubular members originating through the fluid-impervious barrier of the transitional shaft portion and extending through the distal shaft portion;
    a guidewire tubular member having a bore originating from a side aperture and extending beyond the distal shaft portion; and
    a plurality of stiffening members extending from within the fluid-impervious barrier through the transitional shaft portion and into the distal shaft portion.

12. A shaft in accordance with claim 11, wherein the distal end of the distal shaft portion is adapted for connection to a proximal end of a dilation balloon, and the portion of the guidewire tubular member extending beyond the distal end of the distal shaft portion is adapted to pass through the interior of the dilation balloon and to be connected to a distal end of the balloon.

13. A shaft in accordance with claim 11, wherein the distal tubular members are formed of one of a plastic, an elastomer, a metal and a metal alloy.

14. A shaft in accordance with claim 11, wherein the guidewire tubular members is formed of one of a plastic, an elastomer, a metal and a metal alloy.

15. A shaft in accordance with claim 11, wherein the lateral flexibility of the shaft increases toward the distal end of the shaft.

16. A shaft for a balloon dilation catheter to be utilized with a guidewire, the shaft comprising:
    a shaft proximal portion including a proximal tubular member having a bore defining a proximal inflation/deflation lumen;
    a shaft transitional portion connected to a distal end of the shaft proximal portion and including a fluid-impervious barrier;
    a shaft distal portion connected to a distal end of the shaft transitional portion and including a guidewire tubular member, the guidewire tubular member having a bore and extending from a side aperture formed in the shaft distal portion to a point beyond the distal end of the shaft distal portion, the bore of the guidewire tubular member defining a guidewire lumen for conveying a guidewire therethrough;
    a plurality of distal tubular members originating from the fluid-impervious barrier and extending through the shaft distal portion, each distal tubular member having a bore defining a distal inflation/deflation lumen with a proximal end in fluid communication with a distal end of the proximal inflation/deflation lumen; and
    a plurality of stiffening members embedded in the fluid-impervious barrier and extending into the shaft distal portion.

17. A shaft in accordance with claim 16, wherein the stiffening members extend to points disposed between the side aperture and the distal end of the shaft distal portion.

18. A shaft in accordance with claim 16, wherein the distal end of the shaft distal portion is adapted for connection to a proximal end of a dilation balloon, and the portion of the guidewire tubular member extending beyond the distal end of the shaft distal portion is adapted to pass through the interior of the dilation balloon and to be connected to the distal end of the balloon.

19. A shaft in accordance with claim 16, wherein the stiffness of the shaft decreases between the side aperture and the distal end of the shaft distal portion.

20. A catheter in accordance with claim 16, wherein the fluid-impervious barrier is formed with an adhesive and wherein the adhesive surrounds an outside surface of the distal tubular members and an outside surface of the stiffening members with the distal tubular members extending through the adhesive substantially parallel to the stiffening members.

* * * * *